United States Patent [19]

Cyprien et al.

[11] Patent Number: 4,871,547

[45] Date of Patent: Oct. 3, 1989

[54] POLYADDITION SILICONE ELASTOMER DOSAGE FORMS FOR THE CONTROLLED RELEASE OF IODINE VALUES

[75] Inventors: Guy Cyprien, L'Hay les Roses; Alain Fisch, Paris; Johnny Haggiage, Lyons; Hugues Porte, Caluire; Thierry Prazuck, Paris; Ghislaine Torres, Lyons, all of France

[73] Assignee: Rhone-Poulenc Chimie, Courbevoie, France

[21] Appl. No.: 161,173

[22] Filed: Feb. 26, 1988

[30] Foreign Application Priority Data

Feb. 26, 1987 [FR] France ................................ 87 02884

[51] Int. Cl.⁴ ............................................. A61K 31/78
[52] U.S. Cl. ...................................... 424/81; 424/78; 424/150; 424/423; 424/81; 424/667
[58] Field of Search ................. 424/486, 423, 150, 78, 424/81, 423

[56] References Cited

U.S. PATENT DOCUMENTS

| | | |
|---|---|---|
| 2,798,023 | 7/1957 | Berger .................................... 167/81 |
| 3,330,885 | 7/1967 | Dalton et al. ........................ 260/878 |
| 3,992,518 | 11/1976 | Chien et al. ..................... 424/486 X |
| 4,010,259 | 3/1977 | Johansson .......................... 424/150 |
| 4,012,397 | 3/1977 | Schopflin ........................ 128/260 X |
| 4,012,497 | 3/1977 | Schopflin ............................ 128/260 |
| 4,053,580 | 10/1977 | Chien et al. .................... 128/260 X |
| 4,107,346 | 8/1978 | Kravitz ................................ 426/648 |
| 4,155,991 | 5/1979 | Schopflin et al. .............. 128/260 X |
| 4,169,069 | 9/1979 | Unger et al. ..................... 424/486 X |
| 4,196,273 | 4/1980 | Imai et al. ............................. 528/15 |
| 4,230,686 | 10/1980 | Schopflin et al. .............. 424/425 X |
| 4,384,960 | 5/1983 | Polley ............................. 424/150 X |
| 4,447,254 | 5/1984 | Hughes et al. ................. 424/468 X |
| 4,500,337 | 2/1985 | Young et al. ........................... 71/67 |
| 4,559,054 | 12/1985 | Bruck ............................. 424/486 X |

Primary Examiner—Thurman K. Page
Attorney, Agent, or Firm—Burns, Doane, Swecker & Mathis

[57] ABSTRACT

Polyaddition silicone elastomer dosage forms adapted for the continuous and controlled release of iodine values, notably to domestic water supplies for the treatment of the various disease states attributed to iodine deficiency, are shaped from (A) at least one organopolysiloxane containing at least two vinyl groups bonded to silicon per molecule; (B) at least one organopolysiloxane containing at least three hydrogen atoms bonded to silicon; (C) a catalytically effective amount of a platinum group metal compound; and (D) a therapeutically effective amount of at least one water soluble, nontoxic, organic and/or inorganic iodine compound which is in solid or liquid state at ambient temperature and which does not inhibit the catalytic activity of the platinum group metal compound (C).

18 Claims, 4 Drawing Sheets

POLYADDITION SILICONE ELASTOMER DOSAGE FORMS FOR THE CONTROLLED RELEASE OF IODINE VALUES

CROSS-REFERENCE TO COMPANION APPLICATIONS

Our copending applications, Ser. No. 161,443, Ser. No. 161,445, and Ser. No. 161,133, all filed concurrently herewith and all assigned to the assignee hereof.

BACKGROUND OF THE INVENTION

Field of the Invention

The present invention relates to compositions based on polyaddition-curable organopolysiloxanes and containing iodine, to dosage forms shaped therefrom and adapted for the controlled release of iodine values, and to a process for treating domestic water supplies and beverages utilizing such compositions/dosage forms.

Description of the Prior Art

The number of subjects exhibiting a deficiency or an inadequacy of iodine is currently estimated at several hundred million worldwide. The geographical regions affected to the greatest degree are Latin America, particularly along the Andean Cordillera, and virtually all the non-coastal regions of Africa and of Asia (Pakistan, India, Nepal, China, Laos, etc.).

The principal pathological consequences of iodine deficiency are well known. These are essentially, on the one hand, goiter and its complications, among which may be included swallowing disorders, respiratory disorders, cancer, peripheral circulation and, on the other hand, hypothyroidism and its complications, among which may be mentioned: cretinism, cerebral disorders, premature births, miscarriages and congenital abnormalities.

While iodine deficiency has disappeared from industrialized countries because, for example, the salts used for cooking are iodized, this is not the case in the developing countries, where the two main campaigns undertaken to date have proven ineffective.

These campaigns have for their focus, on the one hand:

(i) the iodination of cooking salt: this is not effective in the majority of the developing countries because very frequently the consumption of salt is minimal, the systems for the distribution of salt via the economic and commercial networks are virtually nonexistent and, finally, in a tropical region, iodine which is added to salt escapes rapidly if it is not perfectly packaged; and, one the other hand:

(ii) the intramuscular injection of iodinated oil: this injection has the advantage of exhibiting a delayed action, but it is not devoid of disadvantages, particularly the risks of infection, the risks of iodine allergy, and the risks of hyperthyropidism or of hypothyroidism, which are caused by the injection of a necessarily supraphysiological dosage.

Furthermore, Belgian Pat. No. BE-A-889,680 describes the introduction of oligoelements, including iodine, into the drinking water of ruminants, in the form of a dispersion in a binder such as, for example, plaster of Paris. A diorganopolysiloxane may be added with a view to slowing the diffusion of the oligoelement. In addition, the use of iodine and of iodine compounds for disinfecting or for purifying water is well known. Compare, for example, U.S. Pat. Nos. 2,347,567, 2,743,208 and 3,408,295.

There also exist very many patents describing the use of polymeric systems, especially silicone, for the controlled release of an active ingredient, for example by means of a transdermal system (U.S. Pat. No. 4,053,580), or by oral ingestion, especially for ruminants (French Pat. No. FR-A-2,560,768).

Lastly, U.S. Pat. No. 4,384,960 describes placing iodine $I_2$ tablets in a plastic bottle, into which water enters through a porous polymer membrane. The water dissolves the iodine. The purpose of the membrane is merely to prevent the iodine tablets from leaving the bottle.

It is simply suggested, furthermore, that it is possible to introduce iodine $I_2$ into the bottle in a liquid dispersion of silicone or of a dimethylsiloxane elastomer, and then to cure them. This suggested solution is not technically feasible because, firstly, $I_2$ is a well-known inhibitor of the catalysts for curing silicone elastomers capable of being vulcanized at ambient temperature (see, in particular, the publication by W. D. Morain et al., *Plastic and Reconstructive Surgery*, 59, 2, 215–222 (1977)) and, secondly, because of its high volatility, $I_2$ sublimes during the crosslinking of silicone elastomers when heated.

However, in this system, not only is there no control over the release of iodine, but also the iodination of water takes place by noncontinuous or continuous addition of a few drops of highly iodized (to saturation) water contained in the bottle, to any receptacle containing untreated water. It is clear that the solution proposed by U.S. Pat. No. 4,384,960 is imperfect, especially because of the fact that it involves an individual method which, like the intramuscular injection of iodine, requires mass education and mobilization of entire populations.

SUMMARY OF THE INVENTION

Accordingly, a major object of the present invention is the provision of a polyaddition silicone elastomer composition containing iodine and suitable for use for the continuous treatment of water for domestic purposes, particularly in water supply and treatment systems in wells and boreholes. The subject composition makes it possible to distribute (release) a controlled and measured amount of iodine with a view to ensuring the collective treatment of the various manifestations due to an iodine deficiency, as well as a prophylaxis of these various manifestations.

Another object of the invention is to provide a polyaddition silicone elastomer composition containing iodine which, when suitably immersed in water sources to be treated, especially wells and boreholes, continually distributes (releases), preferably for at least one year, an appropriate amount of iodine in a therapeutically active and effective form and dosage in order to treat the various diseases caused by iodine deficiency.

Yet another object of the invention is to provide a polyaddition silicone elastomer composition containing iodine which, when suitably immersed in water sources to be treated, has no undesirable secondary or side effects which are detrimental to the water to be treated from a chemical and biological standpoint.

Still another object is to provide a silicone composition containing iodine, in a form which is adapted to the environment in which the water to be treated is found, this form being particularly adapted to wells and/or boreholes and offering a system for introduction into the wells and/or boreholes permitting it to be easily replaced.

Another object of the invention is to provide a polyaddition silicone elastomer composition containing iodine which is contributed by an iodine compound which does not inhibit the cure (crosslinking) of the polyaddition silicone composition into an elastomer.

Briefly, the present invention features polyaddition-curable (by hydrosilylation) silicone compositions, comprising:

(A) at least one organopolysiloxane containing at least two vinyl groups bonded to silicon per molecule;

(B) at least one organopolysiloxane containing at least three hydrogen atoms bonded to silicon;

(C) a catalytically effective amount of a catalyst which is a compound of a metal of the platinum group; and (D) an organic and/or inorganic iodine compound in solid or liquid form at ambient temperature, soluble in water, nontoxic and which does not inhibit the catalytic activity of (C).

From 5 to 130 parts, and preferably from 10 to 100 parts of the at least one iodine compound (D) are generally employed per 100 parts of the total amount of organopolysiloxanes (A)+(B).

The amounts of the organopolysiloxanes (A) and (B) are typically selected such that the molar ratio of the hydrogen atoms bonded to silicon in (B) to the vinyl radicals bonded to silicon in (A) generally ranges from 0.4 to 10, preferably from 0.6 to 5.

The vinyl groups in (A) and the hydrogen atoms in (B) are typically bonded to different silicon atoms.

DETAILED DESCRIPTION OF THE PREFERRED EMBODIMENTS OF THE INVENTION

Figure 1:
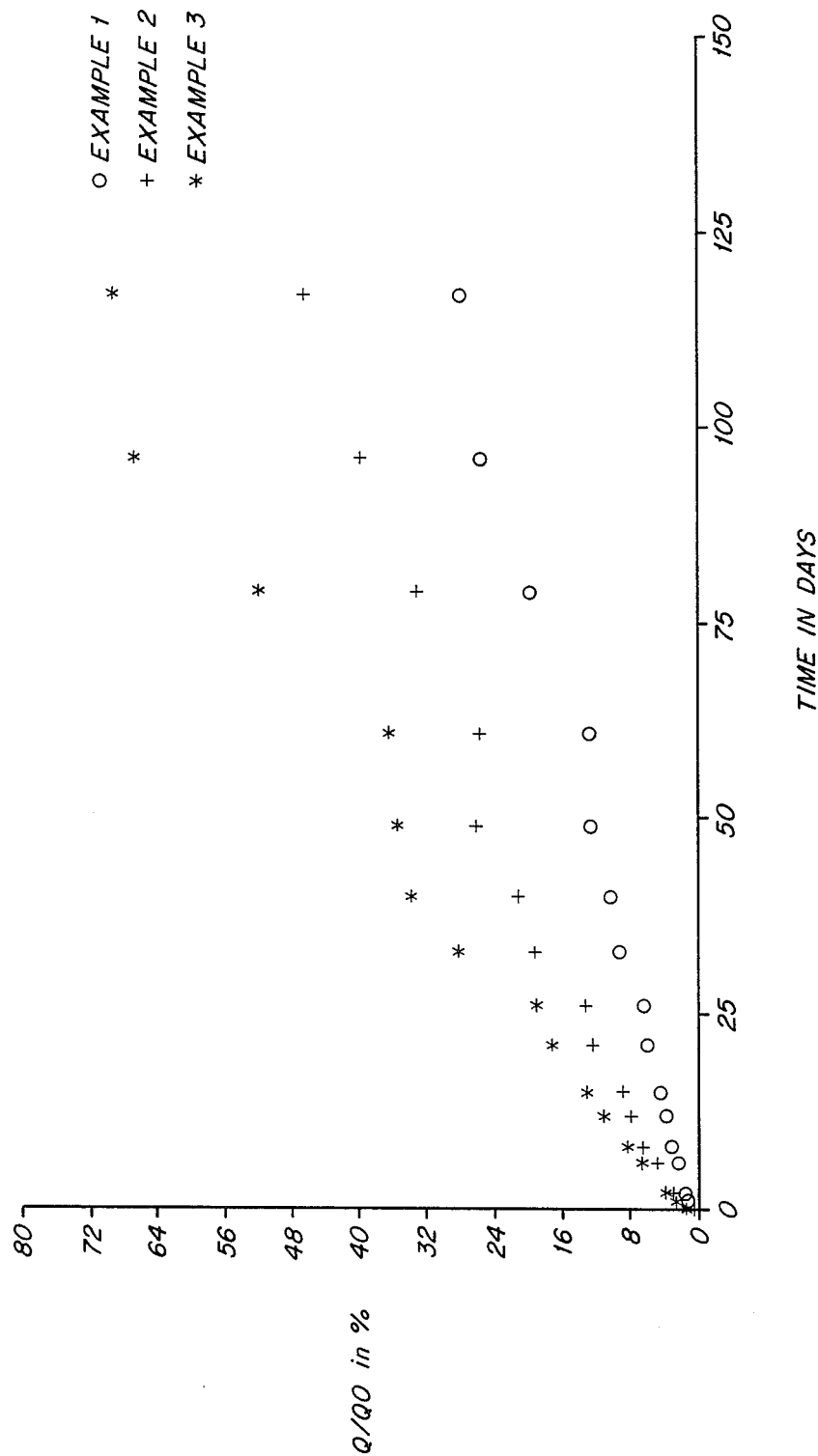
FIGS. 1–4 show the quantity of iodine release relative to the initial amount as a function of time.

More particularly according to the present invention, exemplary of the inorganic iodine compounds, representative are, whether singly or in admixture: iodides or iodates of the general formulae:

$$(M^{a+})(I^-)_a$$

and $$(M^{a+})(IO_3^-)_a$$

in which a is an integer greater than or equal to 1 and M is a cation selected from among an alkali metal such as sodium and potassium, an alkaline earth metal such as magnesium and calcium, a transition metal such as iron and manganese, a quaternary ammonium $(NH_4)^+$, in which the radicals Y, which may be identical or different, are each a linear or branched chain $C_1$–$C_{20}$ alkyl radical or a hydrogen atom, such as the ammonium ion $NH_4^+$.

The cations $M^{a+}$ and $NY_4^+$ are selected such that the corresponding iodide or iodate is a solid or a liquid at ambient temperature, is soluble in water and is nontoxic.

The iodides and iodates which may be employed are particularly those of the formulae:

$NaI$, $NaIO_3$,
$KI$, $KIO_3$,
$MgI_2$, $MgI_2.8H_2O$,
$Mg(IO_3)_2.4H_2O$,
$NH_4I$,
$FeI_2.4H_2O$
$MnI_2$.

These salts may contain water of hydration or water of formation.

As a compound of iodine which is both organic and inorganic, representative is, for example, calcium iodobehenate of the formula:

$$(C_{21}H_{42}ICO_2)Ca$$

Iodinated polyvinylpyrrolidone is exemplary of an organic iodine compound.

For reasons of ease of use, solid iodine compounds are preferred, and $NaI$ and $KIO_3$ are the most preferred among these.

All the iodine compounds such as defined above release iodine in a nontoxic and therapeutically effective form when they are dissolved in the water to be treated.

By "nontoxic iodine compound" according to the invention is intended a compound which, in solution, is not toxic in the dosages contemplated hereby.

By "water-soluble iodine compound" is intended a compound having a solubility of at least 100 μg/1 at ambient temperature.

Furthermore, the iodine compounds (D) must not inhibit the cure of the silicone composition into an elastomer. Molecular iodine $I_2$ is therefore excluded from the iodine compounds (D) capable of being employed according to the present invention.

In the developing countries in particular, water for domestic use (drinking, washing, irrigation, and the like) is essentially provided by structures of two types, wells and boreholes.

For obvious reasons of cost, efficiency and salubriousness, the creation of a new water source is frequently produced by drilling.

A borehole is a column of air drilled through compact rock formations having a depth which is generally between 20 and 100 meters and a diameter of at least approximately 10 cm. Water filters into this column through cracks or various interstices. The water reserve which is immediately available thus consists of a column of 10 to 70 meters, generally from 30 to 50 meters, in height, which is withdrawn with the aid of an immersed-body pump.

This water is renewed chiefly as a function of the use of the borehole, which depends on the season. In fact, in the rainy season the borehole is traditionally used less. On the other hand, in the dry season the borehole is used for approximately 10–12 hours daily, which is a quantity of between 5 and 10 m³ per day for approximately six months.

As a general rule, a well may be run dry twice daily in the dry season, which corresponds to a maximum usage of 5 to 10 m³, based on these average statistical data.

Numerous studies show that in the regions of the world which are highly endemic in goiter, the preexisting proportion of iodine equivalent in the water in boreholes or in wells is less than 2 micrograms per liter (2 μg/1). It is currently estimated that a daily input of approximately 100 μg of iodine equivalent per day per person would be sufficient to prevent the development of endemic goiter and doubtless approximately 150 μg in the presence of regular consumption of goiterogenic substances. Conversely, acute iodine intoxication may be responsible for neurological irritation, for hyperthyroidism or for hypothyroidism.

It is assumed in the medical arts that the ingestion of a dose of 3 grams of iodine equivalent by an adult subject, as a single dose, does not produce any secondary effect.

Consequently, the objective is to make it possible to provide an individual with 20 to 200 μg, preferably approximately 100 μg, of iodine equivalent daily.

Thus, with the knowledge that, on average, an adult individual ingests 2 liters of water daily and on the basis of the above data (a borehole with an output of 600 l/hr), it appears desirable that one liter of treated water should contain approximately 50 μg/l of iodine, which corresponds to 50 μg of iodine equivalent per liter per person, which requires the silicone composition to release 720 mg/d of iodine equivalent, i.e., 270 g of iodine equivalent to be released over one year.

Unless indicated otherwise, the parts and percentages given herein are by weight.

Surprisingly and unexpectedly, it has now in fact been found, according to the present invention, that it is possible to incorporate into a polyaddition silicone elastomer large quantities of iodine compound in a solid or liquid form such as defined above, namely from 5 to 130 parts, preferably from 10 to 100 parts per 100 parts of the total amount of the organopolysiloxane (A)+(B) filled with a reinforcing or semireinforcing siliceous filler, and thus to obtain a crosslinked elastomer which has sufficient mechanical characteristics for the intended application and which makes it possible to ensure a continuous and controlled release of iodine, preferably for at least one year, when immersed in water.

The controlled iodine release system forms parts of the matrix systems in which the diffusion of the active ingredient is normally determined by Fick's Law, that is to say, by diffusion kinetics on the order of ½ for only 60% by weight of the active principal. Beyond 60% the matrix is exhausted and the diffusion fluxes are greatly reduced. Surprisingly and unexpectedly, it has been found that the silicone matrix system according to the invention continuously releases iodine according to zero-order kinetics and does so until 80% by weight and more of the iodine compound has been released.

The considerable advantage contributed by the silicone matrix is, therefore, that it is very easy to extrapolate the continuous diffusion of the active ingredient after a measurement of the quantity released after at least one month, because it it known that the diffusion kinetics are of zero order and that at least 80% of the iodine compound will be released according to these kinetics.

In order to gain complete control of the release of the active ingredient, it is advantageous to shape the silicone matrix in the form of elementary modules (elements) of various shapes such as cubes, right parallelepipeds, cylinders and spheres, whose fundamental parameters are the following:
(a) the nature of the iodine compound;
(b) the mean diameter (particle size) g of the particles of the iodine compound in the preferred case where the latter is a solid;
(c) the concentration of the iodine compound within the matrix;
(d) the surface/volume ratio R of the module.

The nature of the iodine compound and its particle size define the rate of diffusion V of the active ingredient through the matrix.

The lower the value of g, the slower V is and vice versa.

The higher the value of t, the greater the flux of active ingredient and vice versa.

The higher the value of R, the greater the high flux of active ingredient and vice versa.

One skilled in this art, using routine experiments, is capable of rapidly and without difficulty obtaining the required result by extrapolating the theoretical elution time which will correspond to the actual time of diffusion of the active ingredient.

In the case of NaI and KIO₃, which are the preferred iodine compounds, g, t and R may advantageously be within the following ranges:
(i) g of from 1 to 300 μm;
(ii) t of from 10 to 100 parts by weight of iodine compound per 100 parts of (A); and
(iii) R of from 0.5 to 50 in the case of a cylindrical shape.

It is desirable, furthermore, that the iodine compound should be dispersed homogeneously throughout the matrix.

The various bases for the subject polyaddition silicone elastomer compositions, but containing no iodine compound (D), are well known and are described in very many publications and patents. They are available commercially.

These compositions crosslink by an addition reaction (also referred to as a hydrosilylation reaction), catalyzed by a compound of a metal from the platinum group, of a vinyl group of the organopolysiloxane (A) to a hydride functional group of the organopolysiloxane (B).

The vinylated organopolysiloxane (1) may be an organopolysiloxane containing siloxy units of the formula:

in which Y is a vinyl group and Z is a monovalent hydrocarbon group which does not adversely affect the activity of the catalyst. Z is generally selected from among alkyl groups containing from 1 to 8 carbon atoms, inclusive, such as methyl, ethyl, propyl and 3,3,3-trifluoropropyl groups, and aryl groups such as xylyl and tolyl and phenyl, a is 1 or 2, b is 0, 1 or 2, and a+b ranges from 1 to 3. If desired all the other units are units of the average formula:

in which Z is as defined above and c has a value from 0 to 3.

The organopolysiloxane (B) may be an organohydropolysiloxane containing siloxy units of the formula:

in which W is a monovalent hydrocarbon group which does not adversely affect the activity of the catalyst and which has the same definition as Z, d is 1 or 2, e is 0, 1 or 2, d+e has a value from 1 to 3. If desired all the other units are units of the average formula:

$$W_g SiO_{\frac{4-g}{2}} \quad (4)$$

in which W is as defined above, and g has a value from 0 to 3. All of the limiting values of a, b, c, d, e and g are included.

The organopolysiloxane (A) may have a linear, branched, ring or lattice structure. The degree of polymerization is 2 or more and is generally below 5,000. Furthermore, when the organopolysiloxane (A) is linear, it has a viscosity of less than 500,000 mPa.s of 25° C.

Z is generally methyl, ethyl or phenyl radicals, at least 60 mole % of the radicals Z being methyl radicals.

The organopolysiloxanes (A) and (B) are well known to this art and are described, for example, in U.S. Pat. Nos. 3,220,972, 3,284,406, 3,436,366, 3,697,473 and 4,340,709.

Specific examples of siloxy units of formula (1) are the vinyldimethylsiloxy unit, the vinylphenylmethylsiloxy unit, the vinylsiloxy unit and the vinylmethylsiloxy unit.

Specific examples of siloxy units of formula (2) are the $SiO_{4/2}$, dimethylsiloxane, methylphenylsiloxane, diphenylsiloxane, methylsiloxane and phenylsiloxane units.

Specific examples of organopolysiloxanes (A) are dimethylpolysiloxanes with dimethylvinylsiloxy end groups, the methylvinyldimethylpolysiloxane copolymers with trimethylsiloxy end groups, methylvinyldimethylpolysiloxane copolymers with dimethylvinylsiloxy end groups and cyclic methylvinylpolysiloxanes.

The organopolysiloxane (B) may be constituted solely by units of formula (3) or may additionally contain units of formula (4).

The organopolysiloxane (B) may have a linear, branched, ring or lattice structure. The degree of polymerization is 2 or more and is generally less than 5,000.

The group W has the same definition as the group Z above.

Examples of units of formula (3) are: $H(CH_3)_2SiO_{\frac{1}{2}}$, $HCH_3SiO_{2/2}$, $H(C_6H_5)SiO_{2/2}$.

The examples of units of formula (4) are the same as those given above in the case of the units of formula (2).

Specific examples of organopolysiloxanes (B) are: dimethylpolysiloxanes with hydrodimethylsilyl end groups, dimethylhydromethylpolysiloxane copolymers with trimethylsiloxy end groups, dimethylhydromethylpolysiloxane copolymers with hydrodimethylsiloxy end groups, hydromethylpolysiloxanes with trimethylsiloxy end groups and cyclic hydromethylpolysiloxanes.

The ratio of the number of hydrogen atoms bonded to silicon in the organopolysiloxane (B) to the number of groups containing alkenyl unsaturation in the organopolysiloxane (A) ranges from 0.4 to 10, preferably from 0.6 to 5. This ratio may, however, range from 2 to 5, if elastomer foams are produced.

The organopolysiloxane (A) and/or the organopolysiloxane (2) may be diluted in a nontoxic organic solvent which is compatible with silicones.

The organopolysiloxanes (A) and (B) in lattice form are typically designated silicone resins.

The bases for the polyaddition silicone compositions may comprise only linear organopolysiloxanes (1) and (2) such as, for example, those described in the aforementioned U.S. Pat. Nos. 3,220,972, 3,697,473 and 4,340,709, or may at the same time comprise organopolysiloxanes (A) and (B), branched or in lattice form, such as, for example, those described in the aforementioned U.S. Pat. Nos. 3,284,406 and 3,434,366.

The catalysts (C) are also well known to this art.

Rhodium and platinum compounds are preferably employed.

It is possible, in particular, to employ the complexes of platinum and of an organic product described in U.S. Pat. Nos. 3,159,601, 3,159,602, and 3,220,972 and European Pat. Nos. EP-A-57,459, EP-A-188,978 and EP-A-190,530, and the complexes of platinum and vinylated organosiloxane which are described in U.S. Pat. Nos. 3,419,593, 3,715,334, 3,377,432 and 3,814,730.

It is possible, in particular, to use the complexes of rhodium which are described in British Pat. Nos. 1,421,136 and 1,419,769.

The catalyst which is generally preferred is platinum.

In this case, the weight of catalyst (C) calculated as the weight of platinum metal, typically ranges from 2 to 600 ppm, in general from 5 to 200 ppm, based on the total weight of the organopolysiloxanes (A) and (B).

The preferred compositions according to the present invention are those comprising:

(A) 100 parts of a diorganopolysiloxane oil blocked at each end of its polymer chain by a vinyldiorganosiloxy unit in which the organic radicals bonded to the silicon atoms are methyl, ethyl or phenyl radicals, at least 60 mole % of these radicals being methyl radicals, and having a viscosity of 100 to 500,000, preferably from 1,000 to 200,000 mPa.s at 25° C.;

(B) at least one organohydropolysiloxane selected from among linear or lattice liquid homopolymers and copolymers containing, per molecule, at least 3 hydrogen atoms bonded to different silicon atoms and in which the organic radicals bonded to the silicon atoms are methyl and ethyl radicals and at least 60% of these radicals are methyl radicals, the organopolysiloxane (B) being employed in such quantity that the molar ratio of the hydride functional groups to the vinyl groups ranges from 1.1 to 4;

(C) a catalytically effective amount of a platinum catalyst; and (D) an iodine compound such as defined above.

Still more preferably, up to 50% by weight of the polymer (A) is replaced by a lattice copolymer containing trimethylsiloxy, methylvinylsiloxy and $SiO_{4/2}$ units, in which 2.5 to 10 mole % of the silicon atoms bear a vinyl group and in which the molar ratio of the trimethylsiloxy groups to the $SiO_{4/2}$ group ranges from 0.5 to 1.

The compositions according to the invention may additionally comprise reinforcing or semireinforcing or extending fillers (E), which are preferably siliceous fillers.

The reinforcing fillers are selected from the pyrogenic silicas and precipitated silicas. They have a specific surface area, measured according to the BET method, of at least 50 m²/g, preferably greater than 70 m²/g, a mean primary particle size of less than 0.1 micrometer ($\mu$m) and an apparent density of less than 200 g/liter.

These silicas may be incorporated as such or preferably after they have been treated with organosilicon compoudns usually employed for this purpose. These compounds include methylpolysiloxanes such as hexamethyldisiloxane and octamethylcyclotetrasiloxane, methylpolysilazanes such as hexamethyldisilazane and hexamethylcyclotrisilazane, chlorosilanes such as dimethylchlorosilane, trimethylchlorosilane, methylvinyldichlorosilane and dimethylvinylchlorosilane, and alkoxysilanes such as dimethyldimethoxysilane, dimethylvinylethoxysilane and trimethylmethoxysilane. In the course of this treatment, the silicas may increase in their initial weight up to a proportion of 20%, preferably approximately 18%.

The semireinforcing or extending fillers have a particle diameter greater than 0.1 μm and are preferably selected from among ground quartz, calcined clays and diatomaceous earths.

From 5 to 100 parts, preferably from 5 to 50 parts of filler (E) may generally be employed per 100 parts of the total amount of the organopolysiloxanes (A)+(B).

The polyaddition compositions are generally stored in two packs. In fact, they crosslink as soon as all these constituents are mixed. If it is desired to delay this crosslinking in order to obtain good homogenization of the iodine compound, then an inhibitor of the platinum catalyst may be added to the composition. These inhibitors are also well known to this art. It is possible, in particular, to employ organic amines, silazanes, organic oximes, diesters or dicarboxylic acids, acetylenic alcohols, acetylenic ketones, and vinylmethylcyclopolysiloxanes (see, for example, U.S. Pat. Nos. 3,445,420 and 3,989,667). The inhibitor is employed in a proportion of 0.005 to 5 parts, preferably 0.01 to 3 parts, per 100 parts of the constituent (A).

In order to obtain good homogenization of the iodine compound it is desirable, in fact, that the silicone matrix should have a certain viscosity on the order of 5,000 to 30,000 mPa.s at 25° C. A viscosity of this magnitude may be obtained by a precrosslinking, such precrosslinking being arrested at the desired viscosity by the addition of an inhibitor. Sufficient time is thus available in order to homogenize the iodine compound properly within the silicone matrix. The crosslinking is then completed by heating the matrix to a temperature such that the inhibitor no longer has any effect on the catalytic action of the platinum.

The compositions according to the invention may be kneaded could as such and may be extruded or molded in the form of unit modules (elements); the composition may, for example, be molded into the shape of a cylinder with a diameter of from 0.5 to 9 cm. After curing, the silicone composition cylinders which are obtained may be cut to the desired length, in the case of their being employed in boreholes, such that the cylinder contains a sufficient quantity of iodine equivalent for a release over preferably at least one year. At the end of this period, the cylinders are replaced.

Surprisingly, it has been found that these cross-linked silicone compositions have sufficient physical characteristics for the intended applications and release iodine in a continuous and controlled manner over at least one year.

In order to further illustrate the present invention and the advantages thereof, the following specific examples are given, it being understood that same are intended only as illustrative and in nowise limitative. In said examples to follow, reference is made to FIGS. 1 to 4 of the Drawings, which show the quantity of iodine released relative to the initial amount as a function of time.

EXAMPLE 1

Preparation of the component A

The following constituents were homogenized in a kneader at ambient temperature:
(a) 25 parts of a silicone resin containing 40 mole % of $(CH_3)_3SiO_{\frac{1}{2}}$ units, 6 mole % of $(CH_3)(CH_2=CH)SiO_{2/2}$ units and 53.5% of $SiO_{2/2}$ units;
(b) 75 parts of a dimethylpolysiloxane oil blocked by a $(CH_3)(CH_2=CH)SiO_{\frac{1}{2}}$ unit at each end of its polymer chain, having a viscosity of 3,500 mPa.s at 25° C.; and
(c) 40 ppm, calculated as the weight of platinum metal contributed by a 0.25% solution of hexachloroplatinic acid, prepared by stirring, at ambient temperature, 0.6 part of hexachloroplatinic acid, 10 parts of isopropanol, 55 parts of xylene and 6 parts of 1,1,3,3-tetramethyl-1,3-divinyldisiloxane.

Preparation of the component B

The following constituents were homogenized in a kneader at ambient temperature:
(d) 45 parts of a hydrogenated liquid silicone resin prepared by hydrolysis of ethyl silicate and of $(CH_3)_2HSiCl$ in quantities corresponding to one mole of SiO per two moles of $(CH_3)_2HSiCl$ in solution in toluene. This resin had, therefore, a theoretical molar ratio of $(CH_3)HSiO_{\frac{1}{2}}$ units of 2 and an actual molar ratio of 2.23;
(e) 12.5 parts of the resin (a) of component (A), and
(f) 37.5 parts of the vinylated oil (b) of component (A).

The elastomer composition was formulated by mixing 10 parts of the component A with 1 part of the component B.

Preparation of the composition of Example 1

25 parts of NaI having a mean particle size equal to 5 μm were incorporated into 100 parts of the elastomer composition. The mixture was stirred, under vacuum, for 22 minutes at 50° C. When the viscosity of the mixture reached 15,000 mPa.s, the stirring was stopped and the mixture was cast into a mold 23 mm in diameter. The composition was then cured by heating to 100° C.

Experimental protocol for measuring elution kinetics

The elastomeric composition containing NaI was cut to the desired length (50 mm), in accordance with the surface/volume ratio (2.14 cm$^{-1}$) desired to be obtained and was immersed in a container of 600 ml of distilled water, thermostated at 20° C.

The container was equipped with a magnetic stirring system driven in a slow rotary motion (100 rev/min) ensuring the homogeneity of the solution. It was covered with a lid in order to reduce water evaporation to a minimum.

1-ml samples were taken daily during the initial period of elution, and weekly after two weeks of elution.

The concentration of iodide or iodate, released daily, was determined by measurement using an iodide-specific electrode:

Two milliliters of a solution ($K_2SO_4$+ascorbic acid) were added to one milliliter of sample from the container-this solution served as an ion buffer and as a reducing solution in the case where iodates were being measured—together with one milliliter of distilled water. The electrode was immersed in this solution and the electrochemical potential of the solution was measured. A calibration curve established beforehand using iodide solutions containing $5 \times 10^{-5}$ M/l (M: mole) to $5 \times 10^{-2}$ M/l enabled the iodide or iodate concentration (C) to be calculated in mg/l of the solution.

| The characteristics of the immersed cylinder were: | |
| --- | --- |
| Diameter = | 23 mm |
| Height = | 50 mm |
| Surface area = | 44.4 cm$^2$ |
| Volume = | 20.76 cm$^3$ |
| S/V = | 2.14 cm$^{-1}$ |
| Total weight = | 25.52 g |
| Initial quantity of I (Qo) = | 4.27 g |

The results of the elution kinetics are reported in the following Table I.

Cumulative Q corresponds to the quantity of I equivalent (designated "active ion") eluted at time t.

With the knowledge that 80 mole % of the active ion incorporated was eluted in accordance with zero-order kinetics with time, the theoretical elution time was calculated (Te) for each example according to:

$$Te = \frac{0.8 \times Qo}{\text{daily flow}} \text{ (days)}$$

The curve $Q/Qo = f(t)$, and Te of this example are shown in FIG. 1.

TABLE I

| TIME (DAY) | Cumulative Q (gram) active ion | 100*Q/QO % |
| --- | --- | --- |
| 0.12 | 0.013 | 0.29 |
| 0.29 | 0.024 | 0.58 |
| 1.00 | 0.048 | 1.14 |
| 2.00 | 0.063 | 1.48 |
| 6.00 | 0.101 | 2.37 |
| 8.00 | 0.126 | 2.96 |
| 12.00 | 0.158 | 3.72 |
| 15.00 | 0.183 | 4.31 |
| 21.00 | 0.250 | 5.89 |
| 26.00 | 0.270 | 6.35 |
| 33.00 | 0.398 | 9.38 |
| 40.00 | 0.440 | 10.36 |
| 49.00 | 0.542 | 12.76 |
| 61.00 | 0.545 | 12.85 |
| 79.00 | 0.845 | 19.91 |
| 96.00 | 1.098 | 25.87 |
| 117.00 | 1.195 | 28.14 |

EXAMPLE 2

25 parts of NaI having a particle size of from 100 to 200 μm were added to 100 parts of the elastomeric composition prepared in accordance with the procedure of Example 1.

The preparation of the sample was carried out in accordance with the protocol described in Example 1.

A cylinder whose characteristics were as follows was immersed in 500 ml of distilled water, thermostated at 20° C.:

| Diameter = | 23 mm |
| --- | --- |
| Height = | 50 mm |
| Surface area = | 44.4 cm$^2$ |
| Volume = | 20.76 cm$^3$ |
| S/V = | 2.14 cm$^{-1}$ |
| Total weight = | 25.03 cm$^{-1}$ |
| Initial quantity of I (Qo) = | 4.23 g |

The results of the elution kinetics are reported in Table II.

The curve $Q/Qo = f(t)$, and Te of the example are shown in FIG. 1.

TABLE II

| TIME (DAY) | Cumulative Q (gram) active ion | 100*Q/QO % |
| --- | --- | --- |
| 0.12 | 0.020 | 0.47 |
| 0.29 | 0.034 | 0.80 |
| 1.00 | 0.082 | 1.93 |
| 2.00 | 0.106 | 2.49 |
| 6.00 | 0.182 | 4.27 |
| 8.00 | 0.229 | 5.38 |
| 12.00 | 0.284 | 6.67 |
| 15.00 | 0.351 | 8.25 |
| 21.00 | 0.462 | 10.88 |
| 26.00 | 0.539 | 12.68 |
| 33.00 | 0.672 | 15.82 |
| 40.00 | 0.793 | 18.66 |
| 49.00 | 0.941 | 22.15 |
| 61.00 | 1.099 | 25.86 |
| 79.00 | 1.389 | 32.69 |
| 96.00 | 1.627 | 38.30 |
| 117.00 | 1.941 | 45.68 |

EXAMPLE 3

25 parts of NaI having a particle size of from 200 and 400 μm were incorporated in 100 parts of the elastomeric composition prepared in accordance with the procedure of Example 1.

The preparation of the sample was carried out in accordance with the protocol described in Example 1.

A cylinder whose characteristics were as follows was immersed in 500 ml of distilled water, thermostated at 20° C.:

| Diameter = | 23 mm |
| --- | --- |
| Height = | 50 mm |
| Surface area = | 44.4 cm$^2$ |
| Volume = | 20.76 cm$^3$ |
| S/V = | 2.14 cm$^{-1}$ |
| Total weight = | 25.52 g |
| Initial quantity of I (Qo) = | 4.32 g |

The results of the elution kinetics are reported in Table III. The curve $Q/Qo = f(t)$, and Te of the example are shown in FIG. 1.

TABLE III

| TIME (DAY) | Cumulative Q (gram) active ion | 100*Q/QO % |
| --- | --- | --- |
| 0.12 | 0.029 | 0.66 |
| 0.29 | 0.047 | 1.09 |
| 1.00 | 0.109 | 2.51 |
| 2.00 | 0.162 | 3.74 |
| 6.00 | 0.290 | 6.70 |
| 8.00 | 0.352 | 8.14 |
| 12.00 | 0.477 | 11.03 |
| 15.00 | 0.563 | 13.04 |
| 21.00 | 0.738 | 17.07 |
| 26.00 | 0.823 | 19.04 |
| 33.00 | 1.220 | 28.22 |
| 40.00 | 1.465 | 33.89 |
| 49.00 | 1.537 | 35.56 |
| 61.00 | 1.583 | 36.63 |
| 79.00 | 2.250 | 52.06 |
| 96.00 | 2.894 | 66.99 |

TABLE III-continued

| TIME (DAY) | Cumulative Q (gram) active ion | 100*Q/QO % |
|---|---|---|
| 117.00 | 3.004 | 69.52 |

EXAMPLE 4

25 parts of NaI having a particle size of 100–200 μm were incorporated into 100 parts of the elastomeric compositions prepared in accordance with the procedure described in Example 1.

The preparation of the sample was carried out in accordance with the protocol described in Example 1.

A cylinder whose characteristics were as follows was immersed in 1,000 ml of distilled water, thermostated at 20° C.:

| | |
|---|---|
| Diameter = | 36 mm |
| Height = | 50 mm |
| Surface area = | 76.9 cm$^2$ |
| Volume = | 50.9 cm$^3$ |
| S/V = | 1.51 cm$^{-1}$ |
| Total weight = | 60.77 g |
| Initial quantity of I (Qo) = | 10.27 g |

Figure 2:
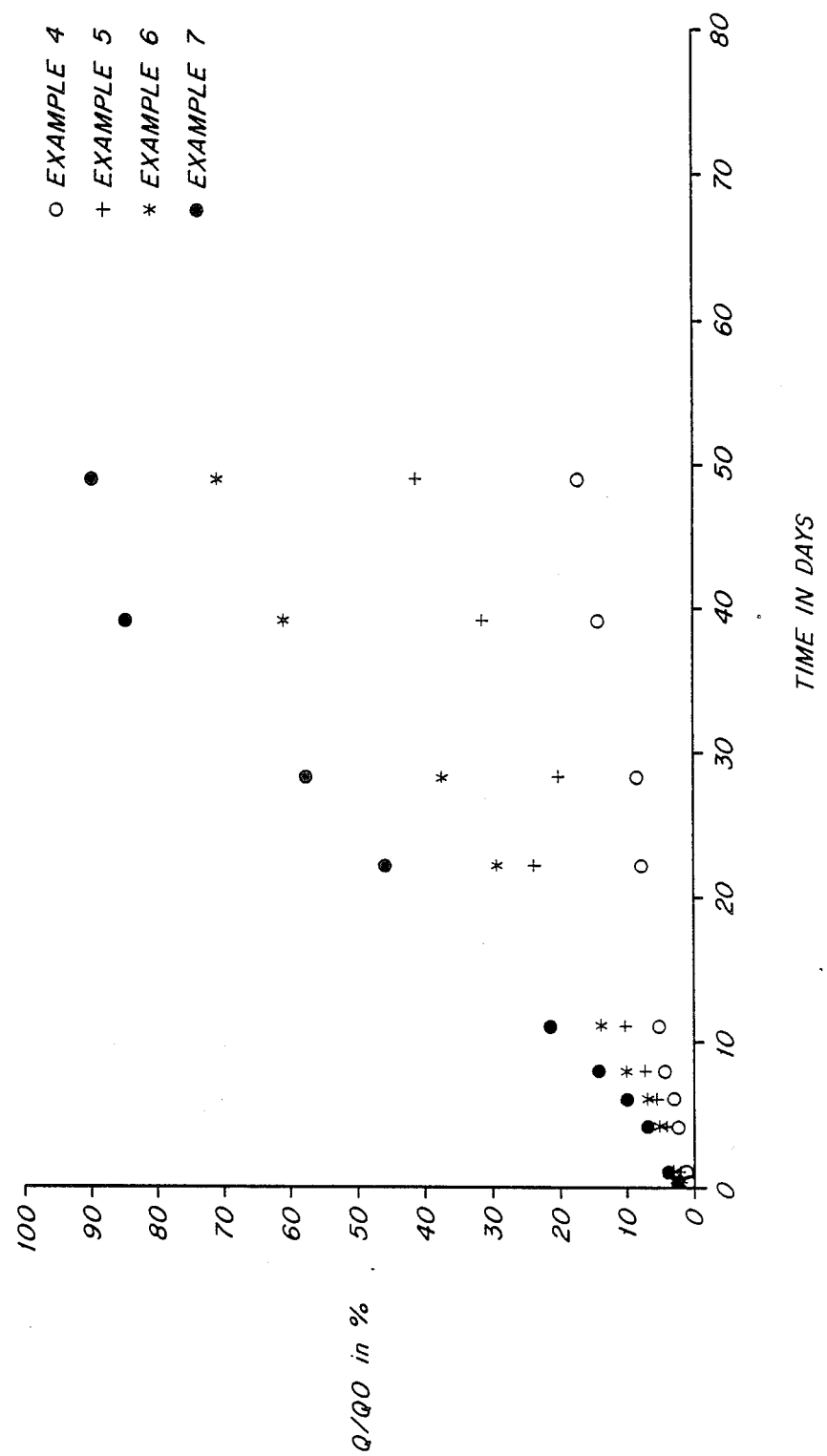

The results of the elution kinetics are reported in Table IV. The curve $Q/Qo=f(t)$, the Te of the example are shown in FIG. 2.

TABLE IV

| TIME (DAY) | Cumulative Q (gram) active ion | 100*Q/QO % |
|---|---|---|
| 0.35 | 0.102 | 0.99 |
| 1.04 | 0.147 | 1.43 |
| 4.10 | 0.245 | 2.38 |
| 6.08 | 0.321 | 3.12 |
| 8.01 | 0.429 | 4.17 |
| 11.06 | 0.549 | 5.34 |
| 22.27 | 0.792 | 7.70 |
| 28.36 | 0.855 | 8.31 |
| 39.20 | 1.462 | 14.21 |
| 49.09 | 1.765 | 17.15 |

EXAMPLE 5

25 parts of NaI having a particle size of 100–200 μm were incorporated into 100 parts of the elastomeric composition prepared in accordance with the procedure defined in Example 1.

The preparation of the sample was carried out in accordance with the protocol described in Example 1.

A cylinder whose characteristics were as follows was immersed in 500 ml of distilled water, thermostated at 20° C.:

| | |
|---|---|
| Diameter = | 16 mm |
| Height = | 50 mm |
| Surface area = | 29.1 cm$^2$ |
| Volume = | 10.03 cm$^3$ |
| S/V = | 2.9 cm$^{-1}$ |
| Total weight = | 11.4 g |
| Initial quantity of I (Qo) = | 1.93 g |

The results of the elution kinetics are reported in Table V. The curve $Q/Qo=f(t)$, the Te of the example are shown in FIG. 2.

TABLE V

| TIME (DAY) | Cumulative Q (gram) active ion | 100*Q/QO % |
|---|---|---|
| 0.35 | 0.029 | 1.51 |
| 1.04 | 0.043 | 2.24 |
| 4.11 | 0.078 | 4.03 |
| 6.08 | 0.107 | 5.52 |
| 8.01 | 0.142 | 7.37 |
| 11.06 | 0.198 | 10.25 |
| 22.28 | 0.460 | 23.85 |
| 28.36 | 0.390 | 20.18 |
| 39.21 | 0.608 | 31.47 |
| 49.10 | 0.800 | 41.42 |

EXAMPLE 6

25 parts of NaI having a particle size of from 100 and 200 μm were incorporated into 100 parts of the elastomeric composition prepared in accordance with the procedure described in Example 1.

The preparation of the sample was carried out in accordance with the operating protocol described in Example 1.

A cylinder whose characteristics were as follows was immersed in 500 ml of distilled water, thermostated at 20° C.:

| | |
|---|---|
| Diameter = | 11.7 mm |
| Height = | 50 mm |
| Surface area = | 20.5 cm$^2$ |
| Volume = | 5.36 cm$^3$ |
| S/V = | 3.82 cm$^{-1}$ |
| Total weight = | 6.4 g |
| Initial quantity of I (Qo) = | 1.08 g |

The results of the elution kinetics are reported in Table VI. The curve $Q/Qo=f(t)$, and Te, are shown in FIG. 2.

TABLE VI

| TIME (DAY) | Cumulative Q (gram) active ion | 100*Q/QO % |
|---|---|---|
| 0.35 | 0.020 | 1.89 |
| 1.04 | 0.031 | 2.88 |
| 4.11 | 0.054 | 4.96 |
| 6.08 | 0.074 | 6.83 |
| 8.01 | 0.107 | 9.90 |
| 11.07 | 0.150 | 13.83 |
| 22.28 | 0.319 | 29.41 |
| 28.36 | 0.405 | 37.35 |
| 39.21 | 0.661 | 60.94 |
| 49.10 | 0.768 | 70.83 |

EXAMPLE 7

25 parts of NaI having a particle size of from 100 to 200 μm were incorporated into 100 parts of the elastomeric composition prepared in accordance with the procedure defined in Example 1.

The preparation of the sample was carried out in accordance with the protocol described in Example 1.

A cylinder whose characteristics were as follows was immersed in 400 ml of distilled water, thermostated at 20° C.:

| | |
|---|---|
| Diameter = | 9.7 mm |
| Height = | 50 mm |
| Surface area = | 16.7 cm$^2$ |
| Volume = | 3.69 cm$^3$ |

-continued

| | |
|---|---|
| S/V = | 4.52 cm$^{-1}$ |
| Total weight = | 4.52 g |
| Initial quantity of I (Qo) = | 0.76 g |

The results of the elution kinetics are reported in Table VII. The curve $Q/Qo=f(t)$, and Te, are shown in FIG. 2.

TABLE VII

| TIME (DAY) | Cumulative Q (gram) active ion | 100*Q/QO % |
|---|---|---|
| 0.35 | 0.017 | 2.22 |
| 1.04 | 0.027 | 3.54 |
| 4.11 | 0.053 | 6.88 |
| 6.08 | 0.075 | 9.83 |
| 8.02 | 0.109 | 14.23 |
| 11.07 | 0.164 | 21.42 |
| 22.29 | 0.351 | 45.92 |
| 28.37 | 0.440 | 57.50 |
| 39.21 | 0.647 | 84.59 |
| 49.10 | 0.686 | 89.68 |

EXAMPLE 8

16.5 parts of NaI having a particle size of 100–200 μm were incorporated into 100 parts of the elastomeric composition prepared in accordance with the procedure described in Example 1.

The preparation of the sample was carried out in accordance with the operating protocol defined in Example 1.

A cylinder whose characteristics were as follows was immersed in 500 ml of distilled water, thermostated at 20° C.:

| | |
|---|---|
| Diameter = | 23 mm |
| Height = | 50 mm |
| Surface area = | 44.4 cm$^2$ |
| Volume = | 20.76 cm$^3$ |
| S/V = | 2.14 cm$^{-1}$ |
| Total weight = | 23.8 g |
| Initial quantity of I (Qo) = | 2.85 g |

Figure 3:
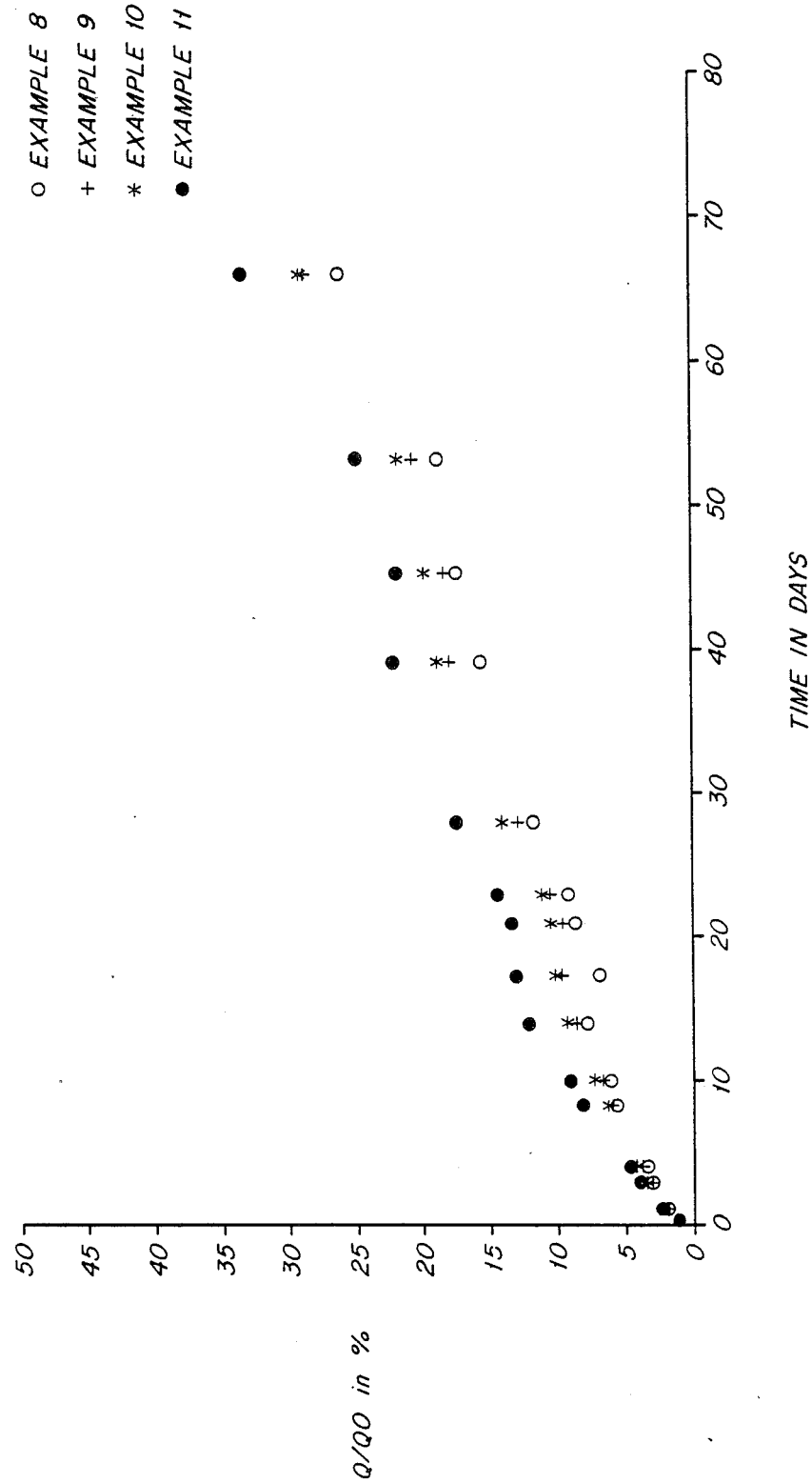

The results of the elution kinetics are reported in Table VIII. The curve $Q/Qo=f(t)$, and Te, are shown in FIG. 3.

TABLE VIII

| TIME (DAY) | Cumulative Q (gram) active ion | 100*Q/QO % |
|---|---|---|
| 0.25 | 0.034 | 1.21 |
| 0.98 | 0.057 | 1.99 |
| 2.91 | 0.088 | 3.08 |
| 3.99 | 0.099 | 3.48 |
| 8.25 | 0.165 | 5.77 |
| 9.97 | 0.174 | 6.09 |
| 13.95 | 0.225 | 7.86 |
| 17.24 | 0.199 | 6.95 |
| 20.95 | 0.249 | 8.71 |
| 22.96 | 0.263 | 9.20 |
| 27.93 | 0.338 | 11.83 |
| 39.14 | 0.451 | 15.79 |
| 45.25 | 0.502 | 17.57 |
| 53.22 | 0.540 | 18.89 |
| 65.96 | 0.752 | 26.34 |

EXAMPLE 9

19 parts of NaI having a particle size of 100 to 200 μm were incorporated into 100 parts of the elastomeric composition prepared in accordance with the procedure defined in Example 1.

The preparation of the sample was carried out in accordance with the protocol defined in Example 1.

A cylinder whose characteristics were as follows was immersed in 500 ml of distilled water, thermostated at 20° C.:

| | |
|---|---|
| Diameter = | 23 mm |
| Height = | 50 mm |
| Surface area = | 44.4 cm$^2$ |
| Volume = | 20.76 cm$^3$ |
| S/V = | 2.14 cm$^{-1}$ |
| Total weight = | 24.34 g |
| Initial quantity of I (Qo) = | 4.12 g |

The results of the elution kinetics are reported in Table IX. The curve $Q/Qo=f(t)$, and Te, are shown in FIG. 3.

TABLE IX

| TIME (DAY) | Cumulative Q (gram) active ion | 100*Q/QO % |
|---|---|---|
| 0.25 | 0.039 | 1.17 |
| 0.98 | 0.067 | 2.02 |
| 2.91 | 0.092 | 2.78 |
| 4.00 | 0.127 | 3.84 |
| 8.26 | 0.201 | 6.09 |
| 9.97 | 0.221 | 6.70 |
| 13.96 | 0.285 | 8.64 |
| 17.25 | 0.320 | 9.69 |
| 20.96 | 0.318 | 9.65 |
| 22.97 | 0.349 | 10.57 |
| 27.95 | 0.428 | 12.99 |
| 39.15 | 0.600 | 18.19 |
| 45.26 | 0.610 | 18.50 |
| 53.23 | 0.693 | 21.01 |
| 65.97 | 0.956 | 28.99 |

EXAMPLE 10

22 parts of NaI having a particle size of 100 to 200 μm were incorporated into 100 parts of the elastomeric composition prepared in accordance with the procedure defined in Example 1.

The preparation of the sample was carried out in accordance with the protocol described in Example 1.

A cylinder whose characteristics were as follows was immersed in 500 ml of distilled water, thermostated at 20° C.:

| | |
|---|---|
| Diameter = | 23 mm |
| Height = | 50 mm |
| Surface area = | 44.4 cm$^2$ |
| Volume = | 20.76 cm$^3$ |
| S/V = | 2.14 cm$^{-1}$ |
| Total weight = | 24.35 g |
| Initial quantity of I (Qo) = | 3.71 g |

The results of the elution kinetics are reported in Table X. The curve $Q/Qo=f(t)$ is shown in FIG. 3.

TABLE X

| TIME (DAY) | Cumulative Q (gram) active ion | 100*Q/QO % |
|---|---|---|
| 0.25 | 0.047 | 1.26 |
| 0.98 | 0.078 | 2.10 |
| 2.91 | 0.126 | 3.38 |
| 4.00 | 0.149 | 3.99 |
| 8.26 | 0.235 | 6.31 |

TABLE X-continued

| TIME (DAY) | Cumulative Q (gram) active ion | 100*Q/QO % |
| --- | --- | --- |
| 9.97 | 0.269 | 7.23 |
| 13.96 | 0.348 | 9.34 |
| 17.24 | 0.375 | 10.07 |
| 20.96 | 0.391 | 10.49 |
| 22.97 | 0.410 | 11.01 |
| 27.94 | 0.522 | 14.03 |
| 39.15 | 0.706 | 18.98 |
| 45.26 | 0.742 | 19.94 |
| 53.22 | 0.819 | 21.99 |
| 65.97 | 1.078 | 28.95 |

EXAMPLE 11

33.3 parts of NaI having a particle size of 100–200 μm were incorporated into 100 parts of the elastomeric composition prepared in accordance with the procedure defined in Example 1.

The preparation of the sample was carried out in accordance with the protocol described in Example 1.

The preparation of the sample was carried out in accordance with the protocol described in Example 1.

A cylinder whose characteristics were as follows was immersed in 500 ml of distilled water, thermostated at 20° C.:

| | |
| --- | --- |
| Diameter = | 23 mm |
| Height = | 50 mm |
| Surface area = | 44.4 cm$^2$ |
| Volume = | 20.76 cm$^3$ |
| S/V = | 2.14 cm$^{-1}$ |
| Total weight = | 25.4 g |
| Initial quantity of I (Qo) = | 5.37 g |

The results of the elution kinetics are reported in Table XI. The curve $Q/Qo = f(t)$, and Te, are shown in FIG. 3.

TABLE XI

| TIME (DAY) | Cumulative Q (gram) active ion | 100*Q/QO % |
| --- | --- | --- |
| 0.25 | 0.069 | 1.29 |
| 0.99 | 0.122 | 2.27 |
| 2.91 | 0.210 | 3.91 |
| 4.00 | 0.250 | 4.65 |
| 8.26 | 0.440 | 8.19 |
| 9.97 | 0.488 | 9.08 |
| 13.97 | 0.656 | 12.20 |
| 17.25 | 0.707 | 13.15 |
| 20.97 | 0.722 | 13.43 |
| 22.97 | 0.782 | 14.54 |
| 27.95 | 0.947 | 17.60 |
| 39.16 | 1.200 | 22.32 |
| 45.26 | 1.187 | 22.08 |
| 53.23 | 1.350 | 25.10 |
| 65.97 | 1.811 | 33.67 |

EXAMPLE 12

25 parts of KIO$_3$ having a mean particle size equal to 5 μm were incorporated into 100 parts of the elastomeric composition prepared in accordance with the procedure defined in Example 1. The mixture was stirred, under vacuum, for 25 minutes at 50° C. When the viscosity of the mixture reached 15,000 mPa.s, the stirring was stopped and the mixture was cast into a mold 23 mm in diameter.

The compostiion was then cured by heating to 100° C. for one hour.

A cylinder whose characteristics were as follows was immersed in 500 ml of distilled water, thermostated at 20° C.:

| | |
| --- | --- |
| Diameter = | 23 mm |
| Weight = | 50 mm |
| Surface area = | 44.4 cm$^2$ |
| Volume = | 20.76 cm$^3$ |
| S/V = | 2.14 cm$^{-1}$ |
| Total weight = | 25 g |
| Initial quantity of I (Qo) = | 2.96 g |

Figure 4:
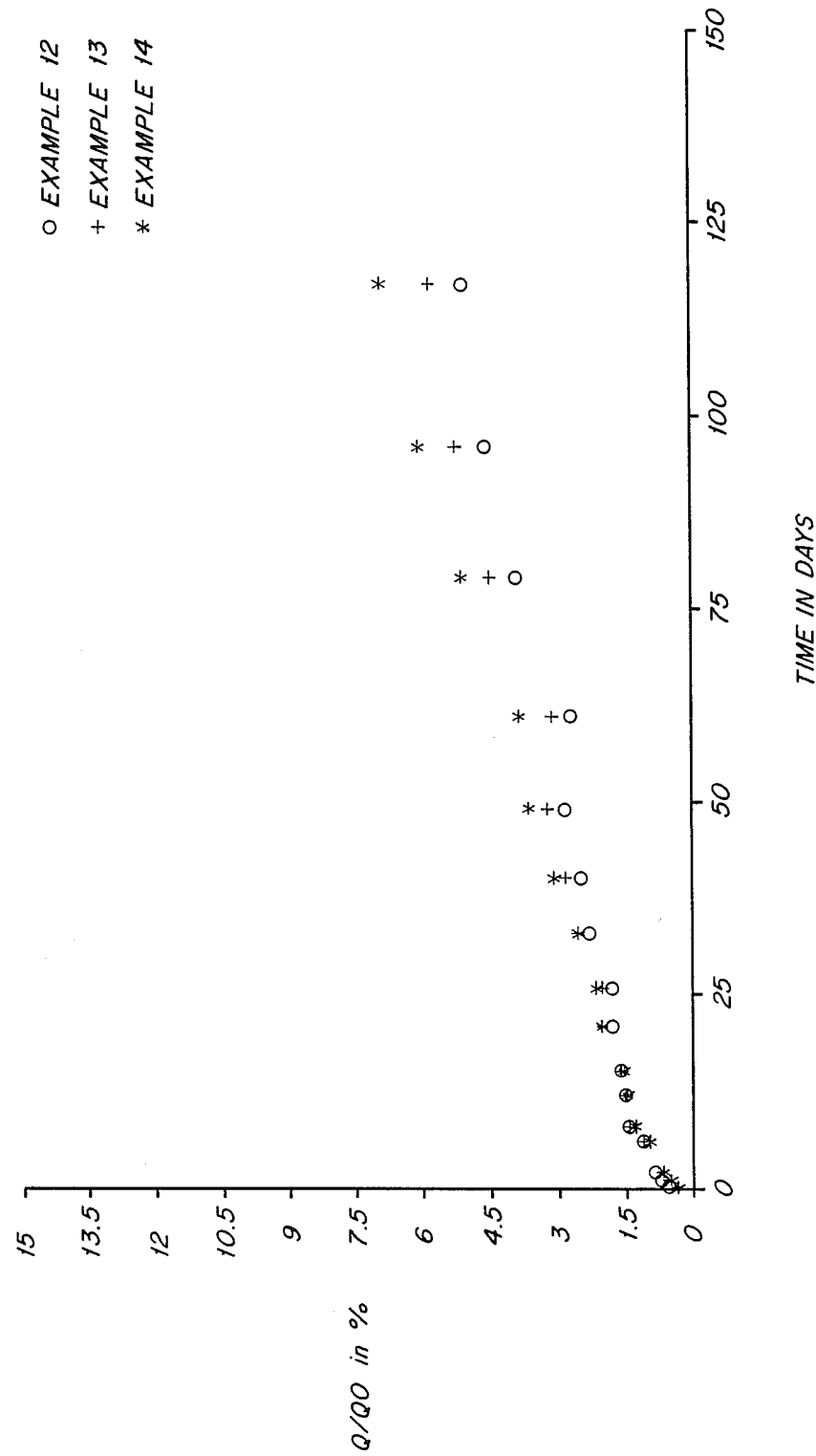

The results of the elution kinetics are reported in Table XII. The curve $Q/Qo = f(t)$, and Te, are shown in FIG. 4.

TABLE XII

| TIME (DAY) | Cumulative Q (gram) active ion | 100*Q/QO % |
| --- | --- | --- |
| 0.12 | 0.007 | 0.25 |
| 0.29 | 0.008 | 0.27 |
| 1.00 | 0.014 | 0.49 |
| 2.00 | 0.019 | 0.64 |
| 6.00 | 0.028 | 0.94 |
| 8.00 | 0.037 | 1.25 |
| 12.00 | 0.043 | 1.47 |
| 15.00 | 0.045 | 1.51 |
| 21.00 | 0.060 | 2.02 |
| 26.00 | 0.064 | 2.15 |
| 33.00 | 0.076 | 2.56 |
| 40.00 | 0.091 | 3.08 |
| 49.00 | 0.108 | 3.65 |
| 61.00 | 0.114 | 3.84 |
| 79.00 | 0.153 | 5.14 |
| 96.00 | 0.180 | 6.08 |
| 117.00 | 0.205 | 6.92 |

EXAMPLE 13

25 parts of KIO$_3$ having a particle size of 100–200 μm were incorporated into 100 parts of the elastomeric composition prepared in accordance with the procedure described in Example 1.

The preparation of the sample was carried out in accordance with the protocol described in Example 12.

A cylinder whose characteristics were identical with those of Example 12 was immersed in 500 ml of distilled water, thermostated at 20° C.

The results of the elution kinetics are reported in Table XIII. The curve $Q/Qo = f(t)$, and Te, are shown in FIG. 4.

TABLE XIII

| TIME (DAY) | Cumulative Q (gram) active ion | 100*Q/QO % |
| --- | --- | --- |
| 0.12 | 0.009 | 0.28 |
| 0.29 | 0.008 | 0.28 |
| 1.00 | 0.014 | 0.47 |
| 2.00 | 0.019 | 0.65 |
| 6.00 | 0.032 | 1.06 |
| 8.00 | 0.042 | 1.39 |
| 12.00 | 0.045 | 1.51 |
| 15.00 | 0.048 | 1.60 |
| 21.00 | 0.060 | 2.01 |
| 26.00 | 0.061 | 2.04 |
| 33.00 | 0.074 | 2.50 |
| 40.00 | 0.086 | 2.87 |
| 49.00 | 0.097 | 3.24 |
| 61.00 | 0.094 | 3.13 |
| 79.00 | 0.135 | 4.51 |
| 96.00 | 0.158 | 5.28 |

TABLE XIII-continued

| TIME (DAY) | Cumulative Q (gram) active ion | 100*Q/QO % |
|---|---|---|
| 117.00 | 0.174 | 5.84 |

EXAMPLE 14

25 parts of $KIO_3$ having a particle size of 200–400 μm were incorporated into 100 parts of the elastomeric composition prepared in accordance with the procedure described in Example 1.

The preparation of the sample was carried out in accordance with the protocol described in Example 13.

A cylinder whose characteristics were identical with those of Example 12 was immersed in 500 ml of distilled water, thermostated at 20° C.

The results of the elution kinetics are reported in Table XIV. The curve $Q/Qo = f(t)$, and Te, are shown in FIG. 4.

TABLE XIV

| TIME (DAY) | Cumulative Q (gram) active ion | 100*Q/QO % |
|---|---|---|
| 0.12 | 0.015 | 0.50 |
| 0.29 | 0.015 | 0.50 |
| 1.00 | 0.022 | 0.73 |
| 2.00 | 0.024 | 0.79 |
| 6.00 | 0.033 | 1.08 |
| 8.00 | 0.042 | 1.38 |
| 12.00 | 0.045 | 1.49 |
| 15.00 | 0.048 | 1.58 |
| 21.00 | 0.055 | 1.82 |
| 26.00 | 0.056 | 1.85 |
| 33.00 | 0.070 | 2.30 |
| 40.00 | 0.076 | 2.51 |
| 49.00 | 0.086 | 2.84 |
| 61.00 | 0.083 | 2.74 |
| 79.00 | 0.119 | 3.94 |
| 96.00 | 0.139 | 4.61 |
| 117.00 | 0.154 | 5.11 |

EXAMPLE 15

40 parts of $KIO_3$ having a particle size of 100–200 μm were incorporated into 100 parts of the elastomeric composition prepared in accordance with the procedure described in Example 1.

The preparation of the sample was carried out in accordance with the protocol described in Example 12.

A cylinder whose characteristics were as follows was immersed in 500 ml of distilled water, thermostated at 20° C.:

| | |
|---|---|
| Diameter = | 23 mm |
| Height = | 50 mm |
| Surface area = | 44.4 cm$^2$ |
| Volume = | 20.76 cm$^3$ |
| S/V = | 2.14 cm$^{-1}$ |
| Total weight = | 27.2 g |
| Initial quantity of I (Qo) = | 4.62 g |

The results of the elution kinetics are reported in Table XV. The calculated TE of this test was 1,760 days.

TABLE XV

| TIME (DAY) | Cumulative Q (gram) active ion | 100*Q/QO % |
|---|---|---|
| 0.25 | 0.031 | 0.66 |
| 0.98 | 0.043 | 0.93 |
| 2.91 | 0.055 | 1.18 |
| 4.00 | 0.059 | 1.28 |
| 8.26 | 0.075 | 1.63 |
| 9.97 | 0.076 | 1.64 |
| 13.96 | 0.087 | 1.87 |
| 17.24 | 0.086 | 1.87 |
| 20.96 | 0.079 | 1.71 |
| 22.97 | 0.082 | 1.76 |
| 27.94 | 0.095 | 2.06 |
| 39.15 | 0.104 | 2.25 |
| 45.25 | 0.118 | 2.55 |
| 53.22 | 0.102 | 2.20 |
| 65.97 | 0.141 | 3.04 |

EXAMPLE 16

25 parts of $KIO_3$ having a particle size of 100–200 μm were incorporated into 100 parts of the elastomeric composition prepared in accordance with the procedure defined in Example 1.

The preparation of the sample was carried out in accordance with the protocol described in Example 12.

A cylinder whose characteristics were as follows was immersed in 200 ml of distilled water, thermostated at 20° C.:

| | |
|---|---|
| Diameter = | 10 mm |
| Height = | 20 mm |
| Surface area = | 8.3 cm$^2$ |
| Volume = | 1.72 cm$^3$ |
| S/V = | 4.8 cm$^{-1}$ |
| Total weight = | 2.04 g |
| Initial quantity of I (Qo) = | 0.242 g |

The results of the elution kinetics are reported in Table XVI. The calculated Te of this test was 530 days.

TABLE XVI

| TIME (DAY) | Cumulative Q (gram) active ion | 100*Q/QO % |
|---|---|---|
| 0.71 | 0.003 | 1.25 |
| 1.71 | 0.004 | 1.72 |
| 4.75 | 0.006 | 2.61 |
| 6.74 | 0.007 | 2.86 |
| 8.71 | 0.008 | 3.37 |
| 11.90 | 0.009 | 3.58 |
| 18.79 | 0.012 | 5.13 |
| 20.72 | 0.012 | 5.05 |
| 33.00 | 0.012 | 4.99 |
| 42.97 | 0.016 | 6.72 |
| 56.00 | 0.021 | 8.97 |
| 77.77 | 0.021 | 8.74 |

EXAMPLE 17

1,020 cylinders of the same composition as that described in Example 16 were immersed in 600 l of distilled water, thermostated at 20° C., circulating at a rate of 600 l/hr.

The initial quantity of I (Qo) was equal to 246.8 g.

A daily flux was actually observed which corresponded to the sum of the fluxes of the elementary cylinders.

The results of the elution kinetics are reported in Table XVII. Te of this test was 530 days.

TABLE XVII

| TIME (DAY) | Cumulative Q (gram) active ion | 100*Q/QO % |
|---|---|---|
| 1 | 4.5 | 1.8 |
| 2 | 7.65 | 3.08 |
| 7 | 12.25 | 4.93 |
| 14 | 16 | 6.44 |
| 24 | 20.25 | 8.15 |
| 30 | 22.5 | 9.06 |
| 40 | 26.25 | 10.57 |
| 50 | 30.12 | 12.13 |
| 60 | 35.0 | 14.1 |
| 70 | 38.75 | 15.6 |
| 80 | 42.5 | 17.1 |
| 90 | 45 | 18.1 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A polyaddition silicone composition curable by hydrosilylation, comprising (A) at least one organopolysiloxane containing at least two vinyl groups bonded to silicon per molecule; (B) at least one organopolysiloxane containing at least three hydrogen atoms bonded to silicon; (C) a catalytically effective amount of a platinum group metal compound; and (D) a therapeutically effective amount of at least one water soluble, nontoxic, organic and/or inorganic iodine compound which is in solid or liquid state at ambient temperature and which does not inhibit the catalytic activity of the platinum group metal compound (C).

2. The silicone composition as defined by claim 1, comprising from 5 to 130 parts by weight of the iodine compound (D) per 100 parts of the organopolysiloxanes (A)+(B).

3. The silicone composition as defined in claim 1, wherein the molar ratio of the hydrogen atoms bonded to silicon in the organopolysiloxane (B) to the vinyl radicals bonded to silicon in the organopolysiloxane (A) ranges from 0.4 to 10.

4. The silicone composition as defined by claim 1, wherein the iodine compound (D) comprises an iodide or iodate of the general formulae:

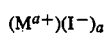

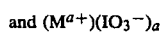

in which a is an integer greater than or equal to 1 and M is an alkali or alkaline earth metal, a transition metal, or a quaternary ammonium $(NY_4)^+$ cation, in which latter the radicals Y, which may be identical or different, are each a linear or branched chain $C_1$-$C_{20}$ alkyl radical or a hydrogen atom.

5. The silicone composition as defined by claim 1, wherein the iodine compound (D) comprises NaI, NaIO$_3$, KI, KIO$_3$, MgI$_2$, MgI$_2$.8H$_2$O, Mg(IO$_3$)$_2$.4H$_2$O, NH$_4$I, FeI$_2$.4H$_2$O or MnI$_2$.

6. The silicone composition as defined by claim 1, wherein the iodine compound (D) comprises calcium iodobehenate.

7. The silicone composition as defined by claim 1, wherein the iodine compound (D) comprises iodinated polyvinylpyrrolidone.

8. The silicone composition as defined by claim 1, comprising:
(A) at least one organopolysiloxane which comprises siloxy units of the formula:

in which Y is a vinyl groupl Z is a monovalent hydrocarbon radical which does not adversely affect the activity of the catalyst (C); a is 1 or 2; b is 0, 1 or 2; and a+b ranges from 1 to 3;
(B) at least one organohydropolysiloxane which comprises siloxy units of the formula:

in which W has the same definition as Z; d is 1 or 2; e is 0, 1 or 2; d+e has a value from 1 to 3;
(C) a catalytically effective amount of a platinum compound; and
(D) an iodine compound.

9. The silicone composition as defined by claim 8, said organopolysiloxane (A) further comprising recurring units of the average formula:

in which c ranges from 0 to 3; and said organohydropolysiloxane (B) further comprising recurring units of the average formula:

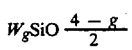

in which g ranges from 0 to 3.

10. The silicone composition as defined by claim 1, comprising:
(A) 100 parts of a diorganopolysiloxane oil blocked at each end of its polymer chain by a vinyl diorganosiloxy unit in which the organic radicals bonded to the silicon atoms are methyl, ethyl or phenyl radicals, at least 60 mole % of these radicals being methyl radicals, and having a viscosity of 100 to 500,000 mPa.s at 25° C.;
(B) at least one organohydropolysiloxane which comprises a linear or lattice liquid homopolymer, or copolymer containing, per molecule, at least 3 hydrogen atoms bonded to different silicon atoms and in which the organic radicals bonded to the silicon atoms are methyl or ethyl radicals and at least 60% of these radicals being methyl radicals, said organohydropolysiloxane (B) being present in such amount that the molar ratio of its hydride functional groups to the vinyl groups of the diorganopolysiloxane oil (A) ranges from 1.1 to 4;
(C) a catalytically effective amount of a platinum catalyst; and
(D) 5 to 130 an iodine compound.

11. The silicone composition as defined by claim 10, comprising, in an amount of up to 50% by weight of the diorganopolysiloxane oil (A), a lattice copolymer which diorganopolysiloxane oil (A), a lattice copolymer which comprises trimethylsiloxy, methylvinylsiloxy and $SiO_{4/2}$ units, in which 2.5 to 10 mole % of the silicon atoms bear a vinyl group and the molar ratio of the trimethylsiloxane groups or the $SiO_{4/2}$ group ranges from 0.5 to 1.

12. The silicone composition as defined by claim 1, further comprising from 5 to 100 parts of reinforcing or semireinforcing siliceous filler material per 100 parts of the organopolysiloxanes (A)+(B).

13. A shaped article comprising the silicone composition as defined by claim 1.

14. The silicone composition as defined by claim 1, in crosslinked elastomeric state.

15. A shaped article comprising the crosslinked elastomeric silicone composition as defined by claim 14.

16. The shaped article as defined by claim 15, adapted to controlledly and continuously release about 50 μg of iodine equivalent per liter, to an external aqueous environment.

17. A method for the treatment, in mammalian organisms in need of such treatment, of disease states attributed to iodine deficiency, comprising adding to the water or beverage supply thereof, at least one shaped article as defined by claim 15, such as to controlledly and continuously release therapeutically effective amounts of iodine equivalent thereto.

18. The silicone composition as defined by claim 1 wherein said iodine compound is dispersed homogeneously throughout the composition.

* * * * *